(12) United States Patent
Chauhan et al.

(10) Patent No.: US 6,582,943 B1
(45) Date of Patent: Jun. 24, 2003

(54) METHOD FOR PRODUCING 2-HYDROXYISOBUTYRIC ACID AND METHACRYLIC ACID FROM ACETONE CYANOHYDRIN

(75) Inventors: Sarita Chauhan, Landenberg, PA (US); Robert DiCosimo, Rockland, DE (US); Robert Fallon, Elkton, MD (US); John Gavagan, Wilmington, DE (US); Leo Ernest Manzer, Wilmington, DE (US); Mark S. Payne, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 10/067,653

(22) Filed: Feb. 5, 2002

(51) Int. Cl.$^7$ ............... C12P 7/42; C12P 7/52; C12P 7/40; C07C 59/00; C07C 57/02
(52) U.S. Cl. ............ 435/146; 430/136; 430/141; 562/579; 562/598
(58) Field of Search ............... 562/579, 598; 435/136, 141, 146

(56) References Cited

U.S. PATENT DOCUMENTS

| | | | |
|---|---|---|---|
| 3,666,805 A | | 5/1972 | Volker et al. |
| 5,223,416 A | | 6/1993 | Endo et al. |
| 5,225,594 A | | 7/1993 | Shima et al. |
| 5,234,826 A | | 8/1993 | Yamagami et al. |
| 5,296,373 A | | 3/1994 | Endo et al. |
| 5,326,702 A | | 7/1994 | Endo et al. |
| 5,508,181 A | | 4/1996 | Hashimoto |
| 5,756,306 A | | 5/1998 | Yamaguchi et al. |
| 6,037,155 A | | 3/2000 | Kobayashi et al. |
| 6,368,804 B1 | * | 4/2002 | Ben-Bassat et al. |

FOREIGN PATENT DOCUMENTS

| | | |
|---|---|---|
| EP | 0610048 | 8/1994 |
| JP | 4040897 A2 | 2/1992 |
| JP | 4-99495 | 3/1992 |
| JP | 4-99496 | 3/1992 |
| JP | 499497 | 3/1992 |
| JP | 4218385 | 8/1992 |
| JP | 5-21987 | 1/1993 |
| JP | 595795 | 2/1993 |
| JP | 5-192189 | 8/1993 |
| JP | 05219969 A2 | 8/1993 |
| JP | 06237776 A2 | 8/1994 |
| JP | 6-237789 | 8/1994 |
| JP | 6284899 | 10/1994 |
| JP | 7-213296 | 8/1995 |

OTHER PUBLICATIONS

W. Bauer, Jr., "Methacrylic Acid and Derivatives" in: Ullmann's Encyclopedia of Industrial Chemistry, 5$^{th}$ Ed.: Eds: Elvers et al., VCH, New York, 1990; vol. A 16., pp 441–452.
A. W. Gross et al., "Methacrylic Acid and Derivatives" in: Kirk–Othmer Encyclopedia of Chemical Technology, 4$^{th}$ Ed.; Eds: J. I. Kroschwitz, M. Howe–Grant; John Wiley and Sons, New York, 1995, vol. 16, pp 474–506.
Asano et al., Agricultural Biological Chemistry, 46: 1164–1165 (1982) (renamed Bioscience, Biotechnology & Biochemistry as of Jan. 1992).
Mowry, Chemical Reviews, 42: 189–284, 1948.
Stewart et al., J. Am. Chem. Soc. 62: 3281–5 (1940).
Japanese Patent Laid–open No. Sho 61–56086.

* cited by examiner

*Primary Examiner*—Juhann Richter
*Assistant Examiner*—Paul A. Zucker

(57) ABSTRACT

The present invention relates to a method for producing 2-hydroxyisobutyric acid where acetone cyanohydrin is converted to 2-hydroxyisobutyric acid using an enzyme catalyst having nitrilase activity, or having a combination of nitrile hydratase and amidase activities. The invention also encompasses production of methacrylic acid wherein the 2-hydroxyisobutyric acid produced with the catalyst described is dehydrated to produce methacrylic acid.

8 Claims, No Drawings

METHOD FOR PRODUCING 2-HYDROXYISOBUTYRIC ACID AND METHACRYLIC ACID FROM ACETONE CYANOHYDRIN

FIELD OF THE INVENTION

This invention is a process to produce 2-hydroxyisobutyric acid using an enzyme catalyst. More specifically, the invention pertains to production of 2-hydroxyisobutyric acid from acetone cyanohydrin using a catalyst having *Acidovorax facilis* 72W nitrilase activity, or having the combined nitrile hydratase and amidase activities of *Comamonas testosteroni* 5-MGAM-4D or of *Comamonas testosteroni* 22-1. The 2-hydroxyisobutyric acid is used as an intermediate to produce methacrylic acid.

BACKGROUND OF THE INVENTION

Methacrylic acid and its esters are widely used to produce acrylic sheet, molding products, coatings, and impact modifiers. It is also used in such products as detergent builders, rheology modifiers, oil additives, solventless inks, paints, and polishes. Several processes to manufacture methacrylic acid exist, but the hydrolysis of methacrylamide sulfate (produced from acetone cyanohydrin) accounts for the majority of current commercial production worldwide (W. Bauer, Jr. "Methacrylic Acid and Derivatives" in: Ullmann's Encyclopedia of Industrial Chemistry, 5$^{th}$ Ed.; Eds: B. Elvers, S. Hawkins, G. Schulz; VCH, New York, 1990; vol. A 16, pp 441–452; A. W. Gross, J. C. Dobson "Methacrylic Acid and Derivatives" in: Kirk-Othmer Encyclopedia of Chemical Technology, 4$^{th}$ Ed.; Eds: J. I. Kroschwitz, M. Howe-Grant; John Wiley and Sons, New York, 1995; vol.16, pp 474–506). In this method, approximately 1.6 kg of sulfuric acid is required to produce 1 kg of methacrylic acid. Therefore, alternatives to eliminate sulfuric acid recycle and regeneration (and the significant energy resources required) in current commercial processes of methacrylic acid production would be highly desirable.

The chemical conversion of 2-hydroxyisobutyric acid to methacrylic acid is disclosed in U.S. Pat. Nos. 3,666,805 and 5,225,594, where 2-hydroxyisobutryic acid is dehydrated using metal oxides and hydroxides, ion exchange resins, alumina, silica, amines, phosphines, alkali metal alkoxides or carboxylates, and where the reaction temperature is typically between 160° C. and 250° C. In a preferred method (U.S. Pat. No. 5,225,594), 2-hydroxyisobutyric acid and sodium hydroxide were reacted at 185° C. to 195° C. under vacuum (300 torr) with stirring, resulting in a 97.1% conversion of 2-hydroxyisobutyric acid, and a 96% yield of methacrylic acid.

An alternative route for methacrylic acid production is hydrolysis of acetone cyanohydrin to 2-hydroxyisobutyric acid using a microbial or enzyme catalyst, followed by dehydration of the 2-hydroxyisobutyric acid to produce methacrylic acid. Various methods for the microbial or enzymatic hydrolysis of α-hydroxynitriles to the corresponding α-hydroxyacids are known. Examples of α-hydroxyacids produced by these methods include glycolic acid, lactic acid, 2-hydroxyisobutyric acid, 2-hydroxy-2-hydroxyphenyl propionic acid, mandelic acid, 2-hydroxy-3, 3-dimethyl-4-butyrolactone, and 4-methylthiobutyric acid.

Microorganisms capable of catalyzing hydrolysis of α-hydroxynitriles include those belonging to the genera Nocardia, Bacillus, Brevibacterium, Aureobacterium, Pseudomonas, Caseobacter, Alcaligenes, Acinetobacter, Enterobacter, Arthrobacter, Escherichia, Micrococcus, Streptomyces, Flavobacterium, Aeromonas, Mycoplana, Cellulomonas, Erwinia, Candida, Bacteridium, Aspergillus, Penicillium, Cochliobolus, Fusarium, Rhodopseudomonas, Rhodococcus, Corynebacterium, Microbacterium, Obsumbacterium, and Gordona. (JP-A-4-99495, JP-A-4-99496 and JP-A-4-218385 corresponding to U.S. Pat. No. 5,223,416; JP-A-4-99497 corresponding to U.S. Pat. No. 5,234,826; JP-A-5-95795 corresponding to U.S. Pat. No. 5,296,373; JP-A-5-21987; JP-A-5-192189 corresponding to U.S. Pat. No. 5,326,702; JP-A-6-237789 corresponding to EP-A-0610048; JP-A-6-284899 corresponding to EP-A-0610049; J P-A-7-213296 corresponding to U.S. Pat. No. 5,508,181.)

Most known methods referenced above for preparing α-hydroxyacids from the corresponding α-hydroxynitriles using enzyme catalysts do not produce and accumulate a product at a sufficiently high concentration to meet commercial needs. This is frequently a result of enzyme inactivation early in the reaction period. For instance, U.S. Pat. No. 5,756,306 teaches that "When an α-hydroxynitrile is enzymatically hydrolyzed or hydrated using nitrilase or nitrile hydratase to produce an α-hydroxyacid or α-hydroxyamide, a problem occurs in that the enzyme is inactivated within a short period of time. It is therefore difficult to obtain the α-hydroxyacid or α-hydroxyamide in high concentration and high yield." (col. 1, lines 49–54).

U.S. Pat. No. 6,037,155 teaches that low accumulation of α-hydroxyacid products is related to enzyme inactivation within a short time after start of the reaction. Enzymatic activity is inhibited in the presence of hydrogen cyanide (Asano et al., *Agricultural Biological Chemistry*, 46:1164–1165 (1982) (renamed *Bioscience, Biotechnology & Biochemistry* as of January 1992)) which is generated in the partial disassociation of α-hydroxynitriles in water, together with the corresponding aldehyde or ketone (Mowry, *Chemical Reviews*, 42:189–284 (1948)). With respect to the production of 2-hydroxyisobutyric acid, acetone cyanohydrin is known to reversibly disassociate to hydrogen cyanide and acetone in water (Stewart et al., *J. Am. Chem. Soc.* 62:3281–5 (1940)), and the resulting hydrogen cyanide can inactivate enzyme activity.

A method for preparing lactic acid, glycolic acid, and 2-hydroxyisobutyric acid by using a microorganism belonging to Corynebacterium spp. is disclosed in Japanese Patent Laid-open No. Sho 61-56086. 2-Hydroxyisobutyric acid has also been produced from acetone cyanohydrin using microorganisms belonging to the genus Rhodococcus, Pseudomonas, Arthrobacter, or Brevibacterium (JP 04040897 A2), and Achromobacter (JP 06237776 A2). The efficiency of 2-hydroxyisobutyric acid production when using *Rhodococcus rhodochrous* (ATCC 19140) was improved by adding acetone at a concentration of 0.5–50 wt % to the reaction mixture (JP 05219969 A2), presumably by sequestration of hydrogen cyanide.

As illustrated above, developing an industrial process using microbial catalysts having nitrilase or nitrile hydratase/amidase activities to efficiently manufacture 2-hydroxyisobutyric acid has proved difficult. The presence of cyanide ion in the reaction mixtures can inactivate or inhibit enzyme activity.

The problem to be solved remains the lack of facile microbial catalysts to convert acetone cyanohydrin to 2-hydroxyisobutyric acid in a process characterized by high selectivity and with high conversions, and with the added advantages of low temperature processing and low waste production relative to previously known methods.

SUMMARY OF THE INVENTION

The invention provides a process for preparing 2-hydroxyisobutyric acid from acetone cyanohydrin with high specificity and at high conversion. The invention includes the steps of (a) contacting acetone cyanohydrin in a suitable aqueous reaction mixture with a catalyst characterized by nitrilase activity (EC 3.5.5.7), or by nitrile hydratase (EC 4.2.1.84) and amidase (EC 3.5.1.4) activities; and (b) isolating the 2-hydroxyisobutyric acid produced in (a) as the acid or corresponding salt. Methacrylic acid is obtained by dehydrating the acid produced in (a); and isolating the acid or corresponding salt. These reactions are shown below.

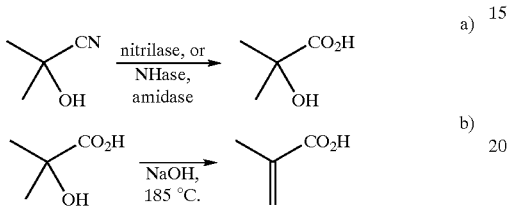

The invention uses enzyme catalysts (including those derived from the biological deposits indicated herein) in the form of intact microbial cells, permeabilized microbial cells, one or more cell components of a microbial cell extract, and partially purified enzyme(s), or purified enzyme(s). In any form, the enzyme catalysts may be immobilized in or on a soluble or insoluble support.

BRIEF DESCRIPTION OF THE BIOLOGICAL DEPOSITS

Applicants have made the following biological deposits under the terms of the Budapest Treaty on the International Recognition of the Deposit of Microorganisms for the purposes of Patent Procedure:

| Depositor Identification Reference | Int'l. Depository Designation | Date of Deposit |
|---|---|---|
| *Acidovorax facilis* 72-PF-17 | ATCC 55745 | 8 Mar. 1996 |
| *Acidovorax facilis* 72W | ATCC 55746 | 8 Mar. 1996 |
| *Acidovorax facilis* 72-PF-15 | ATCC 55747 | 8 Mar. 1996 |
| *Escherichia coli* SS1001 | ATCC PTA-1177 | 11 Jan. 2000 |
| *Escherichia coli* SW91 | ATCC PTA-1175 | 11 Jan. 2000 |
| *Comamonas testosteroni* 22-1 | ATCC PTA-1853 | 10 May 2000 |
| *Comamonas testosteroni* 5-MGAM-4D | ATCC 55744 | 8 Mar. 1996 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

Applicants have solved the stated problem by providing a process to prepare 2-hydroxyisobutyric acid from acetone cyanohydrin with high selectivity and at high conversions by using a catalyst having nitrilase activity, or having a combination of nitrile hydratase and amidase activities. In a subsequent step, 2-hydroxyisobutyric acid is dehydrated to produce methacrylic acid.

A nitrilase (EC 3.5.5.7) enzyme directly converts an aliphatic or aromatic nitrile to the corresponding carboxylic acid without forming the corresponding amide intermediate (Equation 1), whereas nitrile hydratase (NHase) (EC 4.2.1.84) initially converts an aliphatic or aromatic nitrile to an amide, and then the amide is subsequently converted by the amidase (EC 3.5.1.4) to the corresponding carboxylic acid (Equation 2):

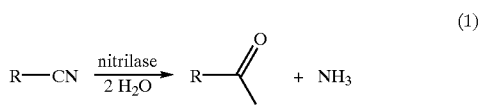

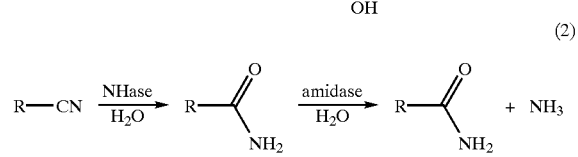

The methacrylic acid produced by the present invention has useful applications in a variety of industries, including as additives and coatings. The method provides the desirable advantages of low temperature processing and low waste production relative to previous known methods.

Definitions

In this disclosure, a number of terms and abbreviations are used. The following definitions apply unless specifically stated otherwise.

The terms "catalyst", "enzyme catalyst", or "microbial cell catalyst" refer to a catalyst that is characterized by a nitrilase activity, or by a combination of nitrile hydratase and amidase activities. The enzyme catalyst may be in the form of an intact microbial cell, permeabilized microbial cell(s), one or more cell components of a microbial cell extract, partially purified enzyme(s), or purified enzyme(s).

The terms "*Acidovorax facilis*" and "*A. facilis*" are used interchangeably.

The terms "*Escherichia coli*" and "*E. Coli*" are used interchangeably.

The terms "*Comamonas testosteroni*" and "*C. testosteroni*" are used interchangeably.

The term "acetone cyanohydrin" is synonymous with 2-hydroxy-2-methyl-propanenitrile, 2-methyl-lactonitrile, α-hydroxyisobutyronitrile; 2-cyano-2-hydroxypropane; 2-cyano-2-propanol, 2-hydroxy-2-cyanopropane, 2-hydroxy-2-methylpropanenitrile, 2-hydroxy-2-methylpropionitrile, 2-hydroxyisobutyronitrile, 2-methyl-2-hydroxypropionitrile, 2-methyllactonitrile, 2-propanone cyanohydrin, dimethyl ketone cyanohydrin, and all other synonyms of CAS Registry Number 75-86-5.

The term "2-hydroxyisobutryic acid" is synonymous with 2-hydroxy-2-methyl-propanoic acid, 2-methyl-lactic acid, α-HIB, α-hydroxy-α-methylpropanoic acid, α-hydroxyisobutanoic acid, α-hydroxyisobutyric acid, 2-hydroxy-2-methylpropanoic acid, 2-hydroxy-2-methylpropionic acid, 2-methyllactic acid, acetonic acid, hydroxydimethylacetic acid, and all other synonyms of CAS Registry Number 594-61-6.

The term "methacrylic acid" is synonymous with 2-methyl-2-propenoic acid, α-methacrylic acid, α-methylacrylic acid, 2-methyl-2-propenoic acid, 2-methylacrylic acid, methylacrylic acid, and all other synonyms of CAS Registry Number 79-41-4.

The term "suitable aqueous reaction mixture" refers to the materials and water in which the acetone cyanohydrin and catalyst come into contact. Components of suitable aqueous reaction mixtures are referred to herein and those skilled in the art appreciate the range of component variations suitable for this process.

The abbreviations in the specification correspond to units of measure, techniques, properties, or compounds as follows: "sec" means second(s), "min" means minutes(s), "h" means hour(s), "d" means day(s), "mL" means milliliters, "L" means liters, "mM" means millimolar, "M" means molar, "mmol" means millimole(s), and "wt" means weight. "HPLC" means high performance liquid chromatography, "ca" means approximately, "O.D." means optical density at the designated wavelength, "IU" means International Units.

DESCRIPTION OF THE PREFERRED EMBODIMENTS

Methods and Materials
Microbial Cell Enzyme Catalysts

The invention for converting acetone cyanohydrin to 2-hydroxyisobutyric acid uses microbial cells characterized by aliphatic nitrilase (EC 3.5.5.7) activity, or by a combination of nitrile hydratase (EC 4.2.1.84) and amidase (EC 3.5.1.4) activities.

A microbial cell possessing all three enzyme activities is *Acidovorax facilis* 72W (ATCC 55746) (U.S. Pat. No. 6,066,490). Microorgansisms characterized by only a nitrilase activity and useful in the process are *Acidovorax facilis* mutants 72-PF-15 (ATCC 55747), and 72-PF-17 (ATCC 55745). Heating a suspension of *Acidovorax facilis* 72W in a suitable buffer at 35–70° C. for between 10 and 120 minutes deactivates the nitrile hydratase and amidase activities of the microbial cell catalyst, without producing a significant decrease in the desired nitrilase activity (U.S. Pat. No. 5,814,508). This heat-treatment produces a catalyst that avoids the formation of the 2-hydroxyisobutyramide, an undesirable byproduct when not completely converted to the corresponding acid. Where the mutants and transformed microbial cells lack the nitrile hydratase and amidase activities of *A. facilis* 72W, no heat-treatment step is needed. Transformed microbial cells containing *A. facilis* nitrilase activity are included in this invention. *Escherichia coli* SS1001 (ATCC PTA-1177) and *Escherichia coli* SW91 (ATCC PTA-1175) are examples of such a transformed microbial cell catalyst that lacks nitrile hydratase and amidase activities.

The invention also uses microbial cells characterized by nitrile hydratase and amidase activities as the enzyme catalyst for converting acetone cyanohydrin to 2-hydroxyisobutyric acid. Preferred microbial catalysts are *Comamonas testosteroni* 5-MGAM-4D (ATCC 55744) and *Comamonas testosteroni* 22-1 (ATCC PTA-1853) and microbial cells transformed to express *Comamonas testosteroni* 5-MGAM-4D or *Comamonas testosteroni* 22-1 nitrile hydratase and amidase activities. *Acidovorax facilis* 72W cells (ATCC 55746) which have not received the heat-treatment step described above may also be used in the invention.

Growth of Microbial Enzyme Catalysts

Microbial strains used for conversion of acetone cyanohydrin were isolated as described below. Frozen 15% glycerol stocks were maintained at −65° C. to −70° C.

*Comamonas testosteroni* 22-1, *Comamonas testosteroni* 5-MGAM-4D, and *Acidovorax facilis* 72W were enriched from soil collected in Orange, Tex., U.S.A., using standard enrichment procedures with E2 basal medium (Table 1) (pH 7.2).

TABLE 1

| E2 Basal Medium g/L | | | |
|---|---|---|---|
| $KH_2PO_4$ | 1.4 | $NaMoO_4.2H_2O$ | 0.0025 |
| $NaH_2PO_4$ | 6.9 | $NiCl_2.6H_2O$ | 0.01 |
| KCl | 0.5 | $CuSO_4.2H_2O$ | 0.005 |
| $MgSO_4.7H_2O$ | 0.5 | biotin | 0.0002 |
| $CaCl_2$ | 0.025 | folic acid | 0.0002 |
| NaCl | 1 | pyridoxine.HCl | 0.001 |
| sodium citrate | 0.1 | riboflavin | 0.0005 |
| $FeSO_4.7H_2O$ | 0.05 | nicotinic acid | 0.0005 |
| $CoCl_2.6H_2O$ | 0.01 | pantothenic acid | 0.0005 |
| $MnCl_2.4H_2O$ | 0.001 | Vitamin B12 | 0.00001 |
| $ZnCl_2$ | 0.0005 | p-aminobenzoic acid | 0.0005 |
| $H_3BO_3$ | 0.000062 | | |

Table 2 contains modifications that were made to the E2 basal medium for the enrichments described above.

TABLE 2

| Strain | Enrichment Nitrile | Other |
|---|---|---|
| *Comamonas testosteroni* 22-1 | 0.2% 3-hydroxyvaleronitrile | 0.6% glycerol |
| *Acidovorax facilis* 72W | 0.2% ethylsuccinonitrile | 0.6% glycerol |
| *Comamonas testosteroni* 5-MGAM-4D | 0.2% 2-methylglutaramide | pH 5.6 |

*Comamonas testosteroni* 22-1 and *Comamonas testosteroni* 5-MGAM-4D were grown aerobically under the following conditions (Table 3) for testing nitrile transformation activity.

TABLE 3

| Strain | Nitrile/ Amide | Medium | ° C. | Time, h |
|---|---|---|---|---|
| 22-1 | 0.1% (v/v) butyronitrile | E2, 1% (w/v) glucose | 30 | 28 |
| 5-MGAM-4D | 0.2% (w/v) propion- amide | E2, 0.6% (w/v) glucose + $Na_2$succinate.$2H_2O$ | 30 | 29 |

*Acidovorax facilis* 72W was grown aerobically under the following conditions (Table 4) for testing nitrile transformation activity. At inoculation, the fermenter contained 8.5 L of Fermenter Medium (Table 4) plus 218 g of Nutrient Feed solution (see below), giving a starting concentration of approximately 7 g/L glycerol. Dissolved oxygen was held at 25% of saturation, at 32° C., and pH at 6.8–7.0. At 18 h post inoculation, feeding of Nutrient Feed solution began. The Nutrient Feed solution included the following components which were sterilized separately and combined after cooling: potassium phosphate, monobasic, 19.6 g in 0.25 L deionized water; magnesium sulfate, heptahydrate, 3.3 g plus sulfuric acid, 4 mL, in 0.15 L deionized water; Trace Metal (Table 6) solution, 67 mL, plus 400 g glycerol in 0.80 L deionized water. Initially, the Nutrient Feed solution was added at a rate of 0.4 g feed/minute (0.15 g glycerol/min). At 26 h, the feed rate was increased to 0.9 g feed/min (0.3 g glycerol/ min). A final increase in feed rate to 1.8 g feed/min (0.6 g glycerol/min) was made at 34 h. 72W Cells were harvested at 58 hours.

TABLE 4

| Component | Stock Concentration | Component | Stock Concentration |
|---|---|---|---|
| Fermenter Medium: | | | |
| Potassium phosphate, monobasic | 0.39 g/L | potassium phosphate, dibasic | 0.39 g/L |
| Difco yeast extract | 5.0 g/L | | |
| Trace Metal Solution: | | | |
| Hydrochloric acid | 10 mL/L | zinc sulfate, heptahydrate | 177 g/L |
| Calcium chloride, dihydrate | 11.4 g/L | sodium molybdate, dihydrate | 0.05 g/L |
| Manganese sulfate, monohydrate | 1.23 g/L | vanadyl sulfate, dihydrate | 0.08 g/L |
| Copper sulfate, pentahydrate | 0.63 g/L | nickel nitrate, hexahydrate | 0.04 g/L |
| Cobalt chloride, hexahydrate | 0.16 g/L | sodium selenite | 0.04 g/L |
| Boric acid | 0.91 g/L | ferrous fulate, heptahydrate | 6.0 g/L |

Harvested cells were frozen at −65 to −70° C. until used for nitrile transformation. For use as an enzyme catalyst having only nitrilase activity, a 10 to 50% (wet cell weight) suspension of *Acidovorax facilis* 72W cells in 0.35 M phosphate buffer (pH 7.0) were first heated to 50° C. for 1 h to inactivate the nitrile hydratase and amidase enzymes present without measurably decreasing the nitrilase activity. *Acidovorax facilis* 72W cells which were not heat-treated at 50° C., and which had nitrilase, and nitrile hydratase and amidase activities, produced yields of 2-hydroxyisobutyric acid and methacrylic acid similar to heat-treated, nitrilase-only containing cells.

Two mutants of the *Acidovorax facilis* 72W (ATCC 55746) strain have been prepared (U.S. Pat. No. 5,858,736, incorporated by reference) which produce only very low levels of the nitrile hydratase activity of the parent strain. These nitrile hydratase-deficient mutant strains derived from *A. facilis* 72W (*Acidovorax facilis* 72-PF-15 (ATCC 55747) and *Acidovorax facilis* 72-PF-17 (ATCC 55745)), do not require heat-treatment of the cells prior to use as an enzyme catalyst for the hydrolysis of acetone cyanohydrin to 2-hydroxyisobutryic acid.

Use of Nitrilase Activity or Nitrile Hydratase/Amidase Activities for Production of 2-Hydroxyisobutyric Acid

*A. facilis* 72W cells contain a nitrile hydratase and an amidase in addition to a nitrilase. The nitrile hydratase produces 2-hydroxyisobutyramide from acetone cyanohydrin, which (if not completely converted to the acid by amidase) could result in the formation of an unwanted byproduct. To avoid this byproduct, the *A. facilis* 72W microbial cell catalyst can be heat-treated to remove the nitrile hydratase and amidase activities to produce a microbial catalyst which gives high selectivity to 2-hydroxyisobutyric acid with no 2-hydroxyisobutyramide production. Enzymatic activity is sustained in a stable state for a prolonged period of time.

Intact microbial cells having nitrilase or nitrite hydratase/amidase activities can be used as catalyst without any pretreatment such as permeabilization. Additionally, the microbial cells may be permeabilized by methods familiar to those skilled in the art (e.g., treatment with toluene, detergents, or freeze thawing) to improve the rate of diffusion of materials into and out of the cells.

The enzyme catalyst can be immobilized in a polymer matrix (e.g., alginate, carrageenan, polyvinyl alcohol, or polyacrylamide gel (PAG)) or on a soluble or insoluble support (e.g., celite) to facilitate recovery and reuse of the catalyst. Methods to immobilize cells in a polymer matrix or on a soluble or insoluble support have been widely reported and are well known to those skilled in the art. The enzyme activity or activities can also be isolated from the microbial cells and used directly as catalyst, or the enzyme activity or activities can be immobilized in a polymer matrix or on a soluble or insoluble support. These methods have also been widely reported and are well known to those skilled in the art (Methods in Biotechnology, Vol. 1: Immobilization of Enzymes and Cells; Gordon F. Bickerstaff, Editor; Humana Press, Totowa, N.J., USA; 1997).

The concentration of enzyme catalyst in the reaction mixture depends on the specific catalytic activity of the enzyme catalyst and is chosen to obtain the desired rate of reaction. The wet cell weight of the microbial cell catalyst in hydrolysis reactions typically ranges from 0.001 g to 0.100 g of wet cells per mL of total reaction volume, preferably from 0.002 g to 0.050 g of wet cells per mL. The specific activity of the microbial cell catalyst (IU/gram wet cell wt.) is determined by measuring the rate of hydrolysis (for nitrilase activity) or hydration (for nitrile hydratase activity) of a 0.10 M solution acetone cyanohydrin at 25° C., using a known weight of microbial cell catalyst. An IU of enzyme activity is defined as the amount of enzyme activity required to convert one micromole of substrate to product per minute.

The temperature of the hydrolysis reaction is chosen to optimize both the reaction rate and the stability of the enzyme catalyst activity. The temperature of the reaction may range from just above the freezing point of the suspension (ca. 0° C.) to 70° C., with a preferred range of reaction temperature of from 5° C. to 35° C. Reactions employing the enzyme catalyst may be run unbuffered in water, or in an aqueous reaction mixture containing a buffer (e.g., sodium or potassium phosphate), where the initial pH of the reaction is between 5.0 and 10.0, and preferably between 6.0 and 8.0. As the reaction proceeds, the pH of the reaction mixture may change due to the formation of an ammonium salt of the 2-hydroxyisobutyric acid from the corresponding nitrile functionality of the acetone cyanohydrin. The reaction can be run to complete conversion of acetone cyanohydrin with no pH control, or in the presence of added buffer to control pH, or a suitable acid or base can be added over the course of the reaction to maintain the desired pH.

Acetone cyanohydrin is known to reversibly disassociate to hydrogen cyanide and acetone in water (Stewart et al., *J. Am. Chem. Soc.* 62: 3281–5 (1940)), and the equilibrium for acetone cyanohydrin is favored as the pH of the reaction mixture decreases. An optimal pH for the enzyme-catalyzed hydrolysis of acetone cyanohydrin is the lowest possible pH at which the enzyme(s) retain activity, typically but not limited to pH 4.5–6.0. Acetone remaining at the end of a reaction may be recovered and used to produce acetone cyanohydrin. Recycling acetone for use as a starting reactant allows for the high overall conversion of acetone cyanohydrin to 2-hydroxyisobutyric acid.

The 2-hydroxyisobutyric acid thus obtained may be isolated by treating the reaction mixture (from which insoluble matter including the cells has been removed) by procedures well known to those of ordinary skill. Such procedures include but are not limited to concentration, ion exchange, distillation, electrodialysis, extraction, and crystallization. The product may be isolated as the ammonium salt, or (after acidification) as 2-hydroxyisobutryic acid.

2-Hydroxyisobutryic acid (or its corresponding salt) may be dehydrated to methacrylic acid by a variety of methods, some of which are described in U.S. Pat. Nos. 3,666,805 and 5,225,594. The dehydration of 2-hydroxyisobutryic acid can be performed using metal oxides and hydroxides, ion exchange resins, alumina, silica, amines, phosphines, alkali metal alkoxides or carboxylates, where the reaction temperature is typically between 160° C. and 250° C.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

In the following Examples, the percent recovery of acetone cyanohydrin and the percent yields of 2-hydroxyisobutyric acid, 2-hydroxyisobutyramide, and acetone were based on the initial concentration of acetone cyanohydrin present in the reaction mixture, and were determined by HPLC using a refractive index detector and a Bio-Rad HPX-87H organic acid analysis column (30 cm×7.8 mm dia.) with pre-column at 50° C. and 0.010 N $H_2SO_4$ as eluent at 1 mL/min.

Example 1

Hydrolysis of Acetone Cyanohydrin to 2-Hydroxyisobutyric Acid by *Comamonas testosteroni* 5-MGAM-4D A suspension of 0.383 g (wet cell paste) *Comamonas testosteroni* 5-MGAM4D cells (ATCC 55744) in 5.56 mL of 50 mM potassium phosphate buffer (pH 6.0) was placed into a 15-mL polypropylene centrifuge tube, then 51.0 mg of acetone cyanohydrin (0.10 M final concentration of acetone cyanohydrin in the suspension) was added and the resulting suspension mixed on a rotating platform at 25° C. Samples for analysis (0.180 mL) were mixed with 0.020 mL of 1.0 M propionic acid (HPLC external standard), centrifuged, and the supernatant analyzed by HPLC for acetone cyanohydrin, acetone, and 2-hydroxyisobutyric acid. After 4 h, the yields of 2-hydroxyisobutyric acid, 2-hydroxyisobutyramide, and acetone were 73.5%, 0%, and 20.4%, respectively, with no acetone cyanohydrin remaining.

Example 2

Hydrolysis of Acetone Cyanohydrin to 2-Hydroxyisobutyric Acid by *Comamonas testosteroni* 22-1

A suspension of 0.343 g (wet cell paste) *Comamonas testosteroni* 22-1 cells (ATCC PTA-1853) in 5.61 mL of 50 mM potassium phosphate buffer (pH 6.0) was placed into a 15-mL polypropylene centrifuge tube, then 51.0 mg of acetone cyanohydrin (0.10 M final concentration of acetone cyanohydrin in the suspension) was added and the resulting suspension mixed on a rotating platform at 25° C. Samples for analysis (0.180 mL) were mixed with 0.020 mL of 1.0 M propionic acid (HPLC external standard), centrifuged, and the supernatant analyzed by HPLC for acetone cyanohydrin, acetone, and 2-hydroxyisobutyric acid. After 21 h, the yields of 2-hydroxyisobutyric acid, 2-hydroxyisobutyramide, and acetone were 40.4%, 0%, and 34.5%, respectively, with 18.4% acetone cyanohydrin remaining.

Example 3

Conversion of Acetone Cyanohydrin to 2-Hydroxyisobutyric Acid by *Acidovorax facilis* 72W A suspension of 0.36 g (wet cell paste) *Acidovorax facilis* 72W cells (ATCC 55746) in 5.58 mL of 100 mM potassium phosphate buffer (pH 6.0) was placed into a 15-mL polypropylene centrifuge tube containing 51.0 mg of acetone cyanohydrin (0.10 M final concentration of acetone cyanohydrin in the suspension), and the resulting suspension mixed on a rotating platform at 25° C. Samples for analysis (0.180 mL) were mixed with 0.020 mL of 1.0 M propionic acid (HPLC external standard), centrifuged, and the supernatant analyzed by HPLC for acetone cyanohydrin, acetone, 2-hydroxyisobutyric acid, and 2-hydroxyisobutyramide. After 22 h, the yields of 2-hydroxyisobutyric acid, 2-hydroxyisobutyramide, and acetone were 22.0%, 0%, and 70.2%, respectively, with 2.5% acetone cyanohydrin remaining.

Example 4

Conversion of Acetone Cyanohydrin to 2-Hydroxyisobutyric Acid by the Nitrilase Activity of *Acidovorax facilis* 72W A suspension of 0.34 g (wet cell paste) *Acidovorax facilis* 72W cells (ATCC 55746) in 5.61 mL of 100 mM potassium phosphate buffer (pH 6.0) was placed into a 15-mL polypropylene centrifuge tube, and the cell suspension heated at 50° C. for 0.5 h (to completely inactivate undesired nitrile hydratase and amidase activities while preserving nitrilase activity), then cooled to 25° C. in a water bath. To the tube was then added 51.0 mg of acetone cyanohydrin (0.10 M final concentration of acetone cyanohydrin in the suspension), and the resulting suspension mixed on a rotating platform at 25° C. Samples for analysis (0.180 mL) were mixed with 0.020 mL of 1.0 M propionic acid (HPLC external standard), centrifuged, and the supernatant analyzed by HPLC for acetone cyanohydrin, acetone, 2-hydroxyisobutyric acid, and 2-hydroxyisobutyramide. After 21 h, the yields of 2-hydroxyisobutyric acid, 2-hydroxyisobutyramide, and acetone were 21.6%, 0%, and 71.3%, respectively, with no acetone cyanohydrin remaining.

Example 5

Conversion of Acetone Cyanohydrin to 2-Hydroxyisobutyric Acid Using *E. coli* Transformant SS1001

A suspension of 0.66 g (wet cell paste) *E. coli* transformant SS1001 (ATCC PTA-1177) in 5.29 mL of 50 mM potassium phosphate buffer (pH 6.0) was placed into a 15-mL polypropylene centrifuge tube, then 51.0 mg of acetone cyanohydrin (0.10 M final concentration of acetone cyanohydrin in the suspension) was added and the resulting suspension mixed on a rotating platform at 25° C. Samples for analysis (0.180 mL) were mixed with 0.020 mL of 1.0 M propionic acid (HPLC external standard), centrifuged, and the supernatant analyzed by HPLC for acetone cyanohydrin, acetone, and 2-hydroxyisobutyric acid. After 8 h, the yields of 2-hydroxyisobutyric acid, 2-hydroxyisobutyramide, and acetone were 23.0%, 0%, and 65.6%, respectively, with no acetone cyanohydrin remaining.

Example 6

Dehydration of 2-Hydroxyisobutyric Acid to Methacrylic Acid

2-Hydroxyisobutyric acid (10 g, 96 mmol), produced according to the procedure described in Example 1, is mixed with sodium hydroxide (0.6 g, 15 mmol) in a flask equipped with overhead stirring and a reflux condenser. After heating the contents of the flask to 185–195° C., additional 2-hydroxyisobutryic acid is added to the reaction mixture continuously at a rate of 5 g/h with stirring and under vacuum (300 torr). The 2-hydroxyisobutyric acid feed additionally contains 0.4 wt % p-methoxyphenol to prevent polymerization of product methacrylic acid. After 24 h, the reaction is stopped, and the selectivity to methacrylic acid is found to be >98% at >97% conversion of 2-hydroxyisobutyric acid, and the methacrylic acid is recovered from the product mixture by distillation.

What is claimed is:

1. A process for producing 2-hydroxyisobutyric acid from acetone cyanohydrin comprising
    (a) contacting acetone cyanohydrin in a suitable aqueous reaction mixture with a catalyst characterized by nitrilase activity derived from *Acidovorax facilis* 72W or by a combination of nitrile hydratase and amidase activities derived from *Comamonas testosteroni*, wherein the catalyst characterized by nitrile hydratase and amidase activity is in the form of microbial cells selected from the group consisting of *Comamonas testosteroni* 5-MGAM4D ATCC 55744 and *Comamonas testosteroni* 22-1 ATCC PTA-1853, and microbial cells transformed to express *Comamonas testosteroni* 5-MGAM-4D ATCC 55744 or *Comamonas testosteroni* 22-1 ATCC PTA-1853 nitrile hydratase and amidase activities; and
    (b) isolating the 2-hydroxyisobutyric acid produced in (a) in the form of a salt or acid.

2. A process for producing methacrylic acid from acetone cyanohydrin comprising
    (a) contacting acetone cyanohydrin in a suitable aqueous reaction mixture with a catalyst characterized by nitrilase activity derived from *Acidovorax facilis* 72W or by a combination of nitrile hydratase and amidase activities derived from *Comamonas testosteroni*, wherein the catalyst characterized by nitrile hydratase and amidase activity is in the form of microbial cells selected from the group consisting of *Comamonas testosteroni* 5-MGAM-4D ATCC 55744 and *Comamonas testosteroni* 22-1 ATCC PTA-1853, and microbial cells transformed to express *Comamonas testosteroni* 5-MGAM-4D ATCC 55744 or *Comamonas testosteroni* 22-1 ATCC PTA-1853 nitrile hydratase and amidase activities;
    (b) dehydrating the 2-hydroxyisobutyric acid produced in (a); and
    (c) isolating the methacrylic acid produced in (b) in the form of a salt or acid.

3. The process of claim 1 or 2, wherein the catalyst characterized by nitrilase activity is in the form of microbial cells selected from the group consisting of *Acidovorax facilis* 72-PF-15 ATCC 55747, *Acidovorax facilis* 72-PF-17 ATCC 55745, microbial cells transformed to express *Acidovorax facilis* 72W nitrilase activity, and *Acidovorax facilis* 72W heated before step (a) to a temperature whereby the nitrile hydratase activity and amidase activity are destroyed and the nitrilase activity is preserved.

4. The process of claim 3 wherein the microbial cells transformed to express *Acidovorax facilis* 72W nitrilase activity are *Escherichia coli* SS1001 ATCC PTA-1177 or *Escherichia coli* SW91 ATCC PTA-1175.

5. A process for producing 2-hydroxyisobutyric acid from acetone Cyanohydrin comprising
    (a) contacting acetone cyanohydrin in a suitable aqueous reaction mixture with a catalyst characterized by nitrilase activity and nitrite hydratase and amidase activities derived from *Acidovorax facilis* 72W; and
    (b) isolating the 2-hydroxyisobutyric acid produced in (a) in the form of a salt or acid.

6. A process for producing methacrylic acid from acetone cyanohydrin comprising
    (a) contacting acetone cyanohydrin in a suitable aqueous reaction mixture with a catalyst characterized by nitrilase activity and nitrile hydratase and amidase activities derived from *Acidovorax facilis* 72W;
    (b) dehydrating the 2-hydroxyisobutyric acid produced in (a); and
    (c) isolating the methacrylic acid produced in (b) in the form of a salt or acid.

7. The process of claim 1, 2, 5, or 6 wherein the catalyst is in the form of intact microbial cells, permeabilized microbial cells, one or more cell components of a microbial cell extract, partially purified enzyme(s), or purified enzyme (s).

8. The process of claim 7 wherein the catalyst is immobilized in or on a soluble or insoluble support.

* * * * *